United States Patent [19]

Knollmueller

[11] 4,086,260
[45] Apr. 25, 1978

[54] ALKOXYSILANE ESTER CLUSTER COMPOUNDS AND THEIR PREPARATION AND USE

[75] Inventor: Karl O. Knollmueller, Hamden, Conn.

[73] Assignee: Olin Corporation, New Haven, Conn.

[21] Appl. No.: 791,359

[22] Filed: Apr. 27, 1977

[51] Int. Cl.² .................... C07F 7/04; C07F 7/18
[52] U.S. Cl. ........................ 260/448.8 R; 252/78.3
[58] Field of Search ........................... 260/448.8 R

[56] References Cited

U.S. PATENT DOCUMENTS

| | | | |
|---|---|---|---|
| 2,881,199 | 4/1959 | Bailey et al. | 260/448.8 R |
| 2,995,591 | 8/1961 | Kovacich et al. | 260/448.8 R |
| 2,995,592 | 8/1961 | Peeler et al. | 260/448.8 R |
| 3,960,913 | 6/1976 | Knollmueller | 260/448.8 R |
| 3,965,135 | 6/1976 | Knollmueller | 260/448.8 R X |
| 3,965,136 | 6/1976 | Knollmueller | 260/448.8 R X |

Primary Examiner—Paul F. Shaver
Attorney, Agent, or Firm—Robert J. Feltovic; Thomas P. O'Day

[57] ABSTRACT

Novel alkoxysilane ester cluster compounds are disclosed. These compounds have the formula:

$$RSi[OSi(OR')_3]_2OR''$$

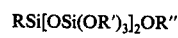

wherein R is hydrogen, an alkyl, alkenyl, aryl or aralkyl group, and each R' and the R'' groups is independently selected from alkyl, alkenyl, aryl and aralkyl with the proviso that at least a majority of the R' radicals are sterically hindered alkyl groups having at least 3 carbon atoms. The preparation of these novel alkoxysilane ester cluster compounds and their use as functional fluids are also disclosed.

14 Claims, No Drawings

ALKOXYSILANE ESTER CLUSTER COMPOUNDS AND THEIR PREPARATION AND USE

BACKGROUND OF THE INVENTION

Silicate esters, silanes, silanols, oxysilanes and oxysilanols are well known in the art for their utility as functional fluids. Many of these compounds previously have been proposed for use as heat transfer fluids, hydraulic fluids, brake fluids, transmission fluids and the like.

In addition, U.S. Pat. No. 3,965,135, issued to the present inventor, discloses alkoxysilanol cluster compounds of the general formula:

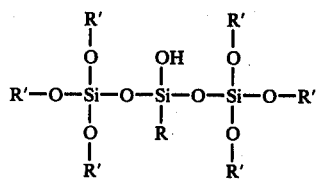

These compounds, defined as silanols, include, by definition, an OH group attached to the central silicon atom. The present compounds are not silanols but rather are silane esters and, hence, do not have such a hydroxy constituent.

Related compounds also are shown in the present inventor's U.S. Pat. No. 3,965,136. This patent illustrates compounds of the general formula:

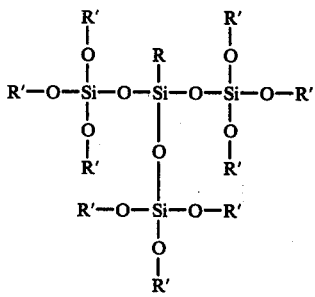

These compounds differ from those of the present invention in that 3 silanoxy radicals are attached to the central silicon atom. The present compounds are silane esters featuring an OR" group attached to the central Si atom.

SUMMARY OF THE INVENTION

Novel alkoxysilane ester cluster compounds, heretofore not described in the literature, have now been developed. These compounds, exhibiting properties rendering them desirable as functional fluids, have the general formula:

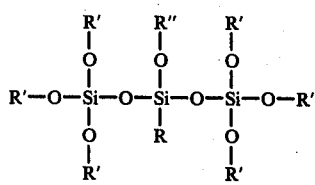

wherein R is hydrogen, an alkyl, alkenyl, aryl or aralkyl group, and each R' and the R" groups is independently selected from alkyl, alkenyl, aryl and aralkyl with the proviso that at least a majority of the R' radicals are sterically hindered alkyl groups having at least 3 carbon atoms. The preparation of these novel alkoxysilane ester cluster compounds and their use as functional fluids have also been developed.

DETAILED DESCRIPTION OF THE PREFERRED EMBODIMENT

The compounds of the present invention are prepared by reacting an alcohol with a halogenated alkoxysilane cluster compound, formed by the reaction of a trialkoxysilanol with a trihalosilane in the presence of an acceptor base, and, preferably, a solvent. Alternatively, under the proper conditions, the novel compounds also can be prepared directly by reacting the trialkoxysilanol with the trihalosilane in the presence of an acceptor base, and, preferably, a solvent, without the separate alcohol-esterification reaction.

The trialkoxysilanol used in forming the halogenated alkoxysilane cluster compound reactant is represented by the formula:

$$HOSi(OR')_3 \qquad II$$

wherein R' groups are independently selected from alkyl, alkenyl, aryl and aralkyl with the proviso that at least a majority of the R' groups are sterically hindered alkyl groups having at least 3 carbon atoms. The preferred groups for R' are alkyl or alkenyl having about 1 to about 24 carbon atoms or aryl or aralkyl having about 6 to about 24 carbon atoms. Preferably, at least a majority of the R' groups are sterically hindered alkyl groups having about 3 to about 24 carbon atoms; most preferably, all of the R' groups are sterically hindered alkyl groups having about 4 to about 12 carbon atoms. Sterically hindered alkyl groups are defined as alkyl radicals which contribute to the hydrolytic stability of the molecule, i.e., which inhibit the reaction of water with the silicon-oxygen or the carbon-oxygen bonds in the molecule. Exemplary of preferred sterically hindered alkyl radicals are non-linear primary alkyl radicals having a beta position side chain of at least 2 carbon atoms, secondary alkyl radicals and tertiary alkyl radicals. Particularly preferred groups include sec. butyl, isobutyl, 2-ethyl butyl, 2-ethyl pentyl, 3-ethyl pentyl, 2-ethyl hexyl, 3-ethyl hexyl, 2,4-dimethyl-3-pentyl and the like.

The trihalosilane used in forming the halogenated alkoxysilane cluster compound reactant used in the present invention is a substituted trihalosilane of the general formula:

$$R-SiX_3 \qquad III$$

wherein R is hydrogen, an alkyl, alkenyl, aryl or aralkyl group. Preferably, R is hydrogen, an alkyl or alkenyl having about 1 to about 18 carbon atoms or an aryl or aralkyl having about 6 to about 24 carbon atoms. Most preferably, R is hydrogen, an alkyl or alkenyl having about 1 to about 8 carbon atoms or an aryl or aralkyl having about 6 to about 14 carbon atoms. The X groups are halogen groups independently selected from F, Cl, Br and I; preferably selected from Cl, Br and I. Most preferred is a trihalosilane reactant wherein X is Cl.

The acceptor base compound may be any compound which will accept hydrogen halide and thereby promote the formation of the intermediates and the cluster compounds of the present invention. Among the preferred acceptor bases are the nitrogenated tertiary organic base compounds having at least 3 carbon atoms, e.g., the lower alkyl and aryl tertiary amines such as triethylamine, tributylamine, as well as pyridine, substituted pyridine, N,N'-dimethylaniline and the like. Pyridine is particularly preferred.

It is preferred to conduct the halogenated alkoxysilane cluster-forming reaction in a solvent medium, in order to moderate the rate of the reaction and accommodate the post-reaction separation of the acceptor base hydrohalide from the product. The solvent medium may be any non-protonic solvent which does not interfere with the reaction. In addition, the reactants (Formula II and III and the acceptor base) must be soluble in the chosen solvent, and the acceptor base hydrohalide must be insoluble in the medium to facilitate its removal from the product. Preferred solvents include benzene, toluene, xylene, hexane, heptane, high-boiling petroleum ethers, and other ethers such as tetrahydrofurane, dioxane and the like. Aliphatic solvents, such as hexane and heptane, are particularly preferred.

The halogenated alkoxysilane cluster compound reactant is represented by the general formula:

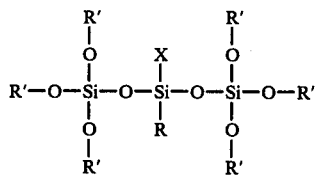   IV wherein X, R and R' are as defined above in Formulas II and III. This cluster compound reactant can be prepared according to Equation A below wherein Z represents the acceptor base and the remaining reactants are as defined above in Formulas II and III:

$$\text{R—SiX}_3 + 2\text{HOSi(OR')}_3 + 2Z \quad\quad\text{(A)}$$

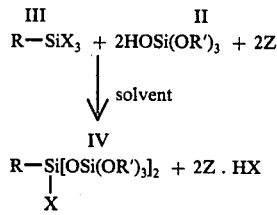

The reaction of Equation A and the products thereof are described in the present inventor's U.S. Pat. No. 3,960,913, the disclosure of which is hereby incorporated by reference in its entirety. While any suitable reaction components proportions may be used, in general, about 1.5 to about 4 moles, preferably about 1.8 to about 2.5 moles, of the trialkoxysilanol is used per mole of trihalosilane. The acceptor base is used in a proportion of about 1.5 to about 4 moles, preferably about 1.8 to about 2.5 moles of the acceptor base per mole of trihalosilane. Use of a solvent is not critical to the reaction. However, it is preferred to use solvent in any suitable amount such as from about 0.5 to about 10 parts of solvent per part by volume of total reactants.

The reaction of Equation A above takes place in a short period of time and a significant amount of reaction product IV is obtained in a matter of minutes. However, to force the reaction to maximum completion, the reaction preferably is allowed to proceed for about 0.5 hours to about 24 hours or longer. Reaction temperature can range from temperatures as low as about −30° C to as high as about 100° C or up to the reflux temperature of the lowest boiling ingredient. In a preferred method, the reactor is initially maintained at about −10° to about 20° C for about 0.5 to 2 hours during addition of reactants, to minimize losses of volatile trihalosilane, and then the reaction is completed at higher temperatures of about 50° to about 100° C for about 0.5 to about 12 hours.

The halogenated alkoxysilane cluster intermediates (product IV) may be used in the product mixture as is, or may be separated from the product mixture by filtrations, distillations or other conventional separation techniques.

The alcohol reactant preferably used in the method of the present invention is represented by the general formula:

$$\text{R''—OH} \quad\quad\quad\quad\quad\quad\quad\quad\quad\quad\quad\quad\text{V}$$

wherein R'' is selected from alkyl, alkenyl, aryl and aralkyl. The preferred groups for R'' are alkyl or alkenyl having about 1 to about 24 carbon atoms or aryl or aralkyl having about 6 to 24 carbon atoms. Preferably, the R'' groups are sterically hindered alkyl groups having about 3 to about 24 carbon atoms; most preferably, having about 4 to 12 carbon atoms. Preferred R'' groups for the alcohol reactant are those as are listed above for the R' group of the trialkoxysilanol reactant of Formula II.

The novel alkoxysilane ester clusters of Formula I can be prepared according to the invention by the reaction outlined in Equation B below:

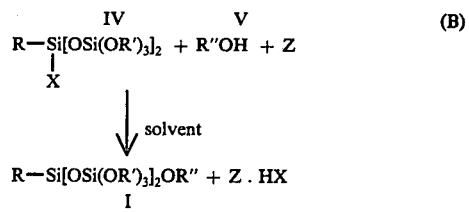

As illustrated by Equation B, the halogenated alkoxysilane intermediate may be reacted with a suitable proportion of an alcohol in the presence of an acceptor base and preferably in a solvent medium, to form the alkoxysilane ester cluster compounds (see Formula I) of the present invention.

The alcohol can be used in any suitable proportion; advantageously it is used in an amount generally ranging from about 0.5 to about 2 moles per mole of halogenated alkoxysilane intermediate IV. Preferably, about 0.9 to about 1.3 and most preferably about 1 to about 1.2 moles of the alcohol is used per mole of the halogenated intermediate. The acceptor base can be used in any suitable amount. Generally, it is used in a proportion of about 0.7 to about 6 or more, preferably about 1 to about 2 and most preferably about 1.1 to about 1.3 moles per mole of the intermediate compound. Use of solvent is not critical to the reaction; but, if used, it can be used in any appropriate amount. It is generally preferred to use solvent in an amount ranging from about 0.3 to about 6 parts, and, most preferably, about 1 to about 3 parts of solvent per part by weight of total reactants.

Reaction temperatures may range from very low temperatures, as low as about −30° C, to very high temperatures, as high as 100° C or up to the reflux temperature of the lowest boiling ingredient. It is generally preferred to initially maintain the reactor at about 20° to about 30° C for about 0.5 to about 2 hours during addition of the reactants, and then complete the reaction at about 50° to about 80° C for about 0.5 to about 24 hours, preferably for about 4 to about 6 hours.

A preferred reaction routine is to first charge the reactor with the halogenated alkoxysilane cluster compound reactant and solvent. Then, the reactor is cooled, and, while stirring the contents, a mixture of the alcohol, acceptor base and solvent is added dropwise. After addition is completed, the reactor temperature is raised and the reaction is driven to completion.

The alkoxysilane ester cluster compound product can be separated from the resulting product mixture by conventional separation techniques such as filtrations and distillations. An advantageous routine is to remove the acceptor base-hydrohalide by filtration, followed by stripping of the solvent medium and fractionation. A preferred separation procedure, using a single reactor, is to water-wash the product mixture and phase-out the acceptor base-hydrohalide-containing aqueous layer. The product solution can then be dried with desiccants, or preferably dried by azeotroping the water with solvent, followed by solvent stripping and fractionation. The desired degree of purity of the final product, of course, determines the choice and extent of the separation method.

An alternate, less desirable reaction route for formation of the novel alkoxysilane ester cluster compounds of the present invention, using the above-described reactants, may be represented by the following equation:

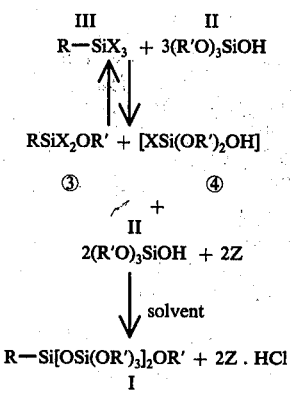

(C)

wherein Z is the acceptor base, and the other reactants are as defined above (see Formulas II and III).

The initial phase of the reaction, outlined in Equation C, is a disproportionation reaction between the trihalosilane and the trialkoxysilanol to form intermediate dismutation products ③ and ④. The dismutation products are unstable and have not been isolated. However, intermediate ③, in the presence of additional trialkoxysilanol, reacts to form the invented cluster compound, shown as product I.

A major competing side reaction also takes place, as outlined in Equation D below, wherein the trihalosilane reactant reacts directly with the trialkoxysilanol reactant, in the presence of the acceptor base, to form the alkoxysilane cluster compound ⑤. This reaction and product is more fully described in the present inventor's U.S. Pat. No. 3,965,136, the disclosure of which is hereby incorporated by reference in its entirety.

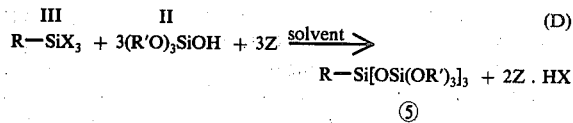

The novel alkoxysilane ester cluster compounds of Formula I above contain an adequate number of silicon atoms to produce good lubricating properties without the need to add additional lubricity improvers. The silicon atoms are shielded by a significant number of sterically hindered alkyl groups to assure protection against attack by water. Accordingly, the invented cluster compounds have been found to have good hydrolytic stability, good lubricating properties and low ASTM viscosity indices. The novel cluster compounds exhibit these properties both in substantially pure form and in mixture with the side product alkoxysilanol clusters as described. According to the present invention, the novel alkoxysilane ester cluster compounds have been found to be particularly useful in functional fluid systems.

The functional fluid systems to which the present invention is directed includes hydraulic-type functional fluid systems and heat transfer-type functional fluid systems.

The hydraulic-type fluid systems include any system wherein a mechanical effort is converted to pressure at a first location, the pressure is transmitted from this first location to a second location via a hydraulic fluid, and the pressure is converted to a second mechanical effort at the second location. Thus, the hydraulic systems contemplated by the present invention include hydraulic brake systems, hydraulic steering mechanisms, hydraulic transmissions, hydraulic jacks and hydraulic lifts. Included among these are the hydraulic systems used in heavy equipment and transportation vehicles including highway and construction equipment, railways, planes and aquatic vehicles. Also included are special or custom fluid-requiring systems such as high pressure or temperature gradient systems including those employed in arctic environments as well as those found in aerospace and lunar vehicles and the like.

The heat transfer-type fluid systems include the hydraulic systems described above wherein heat is dissipated by the hydraulic fluid and include many other systems as well. In general, the present invention contemplates heat transfer systems wherein heat is passed from a first heat conductor at a first location to a heat transfer fluid, the heat is transmitted from the first location to a second location via the heat transfer fluid, and the heat is passed from the heat transfer fluid to a second conductor at the second location. Thus, the heat transfer systems of the present invention include heat dissipation systems, fluidic heating systems, e.g., radiator-type circulating fluid heating systems, heat exchange systems such as gas-liquid and liquid-liquid concurrent and countercurrent tubular heat exchangers as are used, for example, in the chemical process industries, cooling systems for nuclear reactors, radiator-type cooling systems, and any other temperature gradient systems in which a closed or sealed fluid heat transfer medium is used.

In the functional fluid systems of the present invention, the compounds of Formula I above are used in an effective amount. Due to the particularly advantageous hydrolytic stability of these compounds, as well as their high lubricity, high viscosity index, and low viscosity at low temperatures, the compounds may be used without any additives or diluents. Thus, by an effective amount of these compounds is meant the compound product without additional fluid components as well as fluids containing additional fluid components. In one embodiment, the compounds of Formula I may be employed without additives or diluents. Alternatively, these compounds may comprise the base component of a functional fluid or may constitute a minor component, e.g., an additive, in a functional fluid containing a different base component. In general, an effective amount may be any amount which will produce the desired fluid characteristics for a given system. Therefore, as little as 5% or less of one or more of the compounds of Formula I may be used or as much as about 100% of the compounds may be used, percentages by weight. For example, 20 to about 95% or about 100% of the functional fluid may be one or more of the compounds of Formula I, e.g., 45 to 90% of the fluid may comprise one or more compounds of Formula I.

Various diluents, inhibitors and other additives are well known in the functional fluid art and these may optionally be added to the functional fluids used in the systems of the present invention, if desired. For example, a diluent component may be one or more glycol monoethers or diethers of the formula:

$$R_1[O-R_2]_xOR_3 \qquad V$$

wherein $R_1$ is an alkyl of 1 to 4 carbon atoms; $R_2$ is alkylene of 2 to 4 carbon atoms; $R_3$ is hydrogen or an alkyl of 1 to 4 carbon atoms; and $x$ is an integer from 2 to 4. The $R_1$, $R_2$ and $R_3$ groups may be straight chained or branched and the alkylene oxide group $OR_3$ in the above formula may comprise mixtures of alkylene oxides. Also included among the possible diluents are one or more glycols, such as the alkylene glycols, having the formula:

$$HO(R_4O)_yH \qquad VI$$

wherein $R_4$ is an alkylene of 2 to 3 carbon atoms and $y$ is an integer from 1 to 5.

Illustrative of the above-described diluents are the following: diethylene glycol monoethyl ether, diethylene glycol monobutyl ether, triethylene glycol monomethyl ether, triethylene glycol monoethyl ether, tetraethylene glycol monomethyl ether, ethylene glycol, propylene glycol, diethylene glycol and tetraethylene glycol. Various other diluents and mixtures thereof, which are well known in the art may also be used with the organosilane containing base component of this invention. U.S. Pat. No. 3,377,288 discloses various diluents which may be utilized.

Generally, the particular amount of diluents which is used is not critical and widely varying amounts may be used. More particularly, the diluent components may constitute from 0 up to about 80% by weight of the fluid and preferably from about 20 to about 60%.

Various additives may be added to the fluids used in the systems of this invention to control or modify various chemical and physical properties. Among the various types of additives which can be added to the fluids are included inhibitors for pH and corrosion control, antioxidants, rust inhibitors, viscosity index improvers, pour point depressants, lubricating additives, antifoamants, stabilizers, vapor phase corrosion inhibitors, rubber swelling adjusters, demulsifiers, dyes and odor suppressants. Generally, the total amount of additives which may be incorporated into the fluid composition will vary between about 0 to about 20%, e.g., from about 0.1 to 8% and more specifically from about 0.2 to about 5% by weight, based on the total weight of the fluid composition.

For example, alkaline inhibitors for pH and corrosion control may optionally be employed in an amount sufficient to maintain alkaline conditions in the fluid compositions, e.g., at an apparent pH value of from about 7 to about 11.5, if desired. These inhibitors may generally be added in an amount of from about 0 to about 8% by weight based on the total weight of fluid compositions, e.g., from about 0.5 to about 6%. Useful alkaline inhibitors include, for example, alkali metal salts of higher fatty acids such as potassium oleate, the potassium soap of rosin or tall oil fatty acids, amines such as morpholine and ethanolamine and amine salts such as mono- or dibutyl ammonium borates.

An antioxidant may optionally be used, if desired. Typical antioxidants include, 2,2-di(4-hydroxyphenyl) propane, phenothiazine, amines such as phenylalphanaphthylamine and hindered phenols such as dibutyl cresol. Generally, the amount of antioxidant used will vary from 0 to about 3% by weight, e.g., from about 0.001 to about 2% by weight based on the total weight of the fluid composition.

Additionally, other additives, if desired, may be incorporated into the fluid composition. For example, corrosion inhibitors such as butynediol and rubber swelling adjusters such as dodecyl benzene may be used.

The above-noted inhibitors and additives are merely exemplary and are not intended as an exclusive listing of the many well-known materials which can be added to fluid compositions to obtain various desired properties. Other illustrations of additives and diluents which may be used can be found in U.S. Pat. No. 3,377,288 and in "Introduction to Hydraulic Fluids" by Roger E. Hatton, Reinhold Publishing Corp. (1962).

The following examples depict various embodiments of the present invention; they are intended to be illustrative and not limiting in nature. All parts and percentages are by weight unless otherwise specified.

Preparation of Halogenated Alkoxysilane Intermediate

A two-liter, three-neck flask is equipped with a stirrer, reflux condenser, thermometer and an equilibrated dropping funnel. Provisions are made to change quickly from a cooling bath to a heating mantle without disturbing the apparatus. To prevent moisture from entering, the reflux condenser is topped with a $CaCl_2$ tube, while a slow stream of dry nitrogen is passed through the apparatus via the equilibrated funnel.

The flask is charged with 107.4 g, $CH_3SiCl_3$ (0.718 mole) and 554 ml toluene and is cooled to ~0° C with ice. The dropping funnel is charged with a mixture of 400 g (sec. $C_4H_9O)_3SiOH$, purity 95% (effectively 380 g silanol or 1.437 moles) and 113.7 g pyridine (1.437 moles). The silanol/pyridine solution is dropped into the methyltrichlorosilane at such a rate so as to maintain the temperature between 0° and +3° C. About 1¼ hours are required for the addition, after which time the mixture is heated for 2 hours at 60° C. To ease the stirring, 200 ml more toluene are added and the mixture is allowed to cool to room temperature.

In order to prepare a stock solution for subsequent reactions, the pyridinium chloride is filtered and washed with toluene. The combined filtrate and wash, hereinafter called the stock solution, has a volume of 1330 ml. Based on Vapor Phase Chromatography (VPC) data, the product $CH_3Si[OSi(OC_4H_9)_3]_2Cl$ is present in 70% by weight yield, based on solvent-free substrate.

PREPARATION OF ALKOXYSILANE ESTER CLUSTER COMPOUNDS

Example 1

Using the apparatus set up for the preparation of the intermediate, 665 ml of the prepared stock solution (containing the equivalent of 0.359 mole, $CH_3SiCl_3$ and 0.719 mole silanol) is charged into the flask and cooled to 0° C. A mixture of 35.4 g sec. butanol (0.477 mole) and 36 g pyridine (0.455 mole) (a slight excess over the theoretically required 26.61 g sec. butanol and 28.39 g pyridine (each 0.359 mole)) is charged into the dropping funnel and added at 0° C. The observed heat effect is small. To complete the reaction, the mixture is heated 4 hours at 60° C and allowed to cool overnight. The pyridinium chloride is washed out in 4 washes, 200 ml water each, separating the organic and aqueous phases by syphoning. After the last wash, the wash water is chloride free. Residual water is removed using a Dean Stark Trap by azeotroping off the water. The solvent is next removed by distillation; final stripping is done under vacuum at 80° C.

The crude weight of product is 213 g. It is fractionated in a micro Vigreux column. After a forecut of b.p. 125°–151° C/0.02–0.05 mm, weighing 30 g (cut I), the product boils at 151° C/0.02 mm; 161° C/0.07 mm, and is obtained in an amount of 144.9 g (cut II). In a late cut, b.p. 162°–191° C, 29.9 g product is collected, containing higher boilers including cluster. 5.5 g residue remains in the pot.

Based on $CH_3SiCl_3$ charged, the in-hand yield of cut II is 62.7%.

The product $CH_3$-$Si[OSi(OC_4H_9)_2]_2OC_4H_9$ is 98% pure by VPC. The generic formula for the product, $C_{29}H_{66}O_9Si_3$, is calculated to contain the components:
C = 54.16%: H = 10.35%: Si = 13.10%.
The actual product was analyzed to contain:
C = 54.14%: H = 10.21%: Si = 13.18%.

EXAMPLE 2

Using the conditions of Example I and reacting the remaining 665 ml stock solution (0.359 mole, $CH_3Si_3Cl_3$ equivalent) with 60 g 2-ethyl hexanol, $C_8H_{17}OH$, and 45 g pyridine (which is an excess over the theoretically required 46.75 g 2-ethyl hexanol and 28.39 pyridine (0.359 mole each)) with an identical work up, affords upon distillation of the 225.8 g crude product:

| | | |
|---|---|---|
| Cut I | 23.2 g | b.p. 116–151° C/0.05 mm (mostly excess 2-ethyl hexanol) |
| Cut II | 21.3 g | b.p. 158–165° C/0.05 mm |
| Cut III (main cut) | 156.1 g | b.p. 180° C/0.05 mm |
| Residue | 26.1 g | |

Based on $CH_3SiCl_3$ charged, the product of cut III, the desired product $CH_3$-$Si[OSi(OC_4H_9)_3]_2OC_8H_{17}$, is obtained in 62.2% yield.

The product has a generic formula of $C_{33}H_{74}O_9Si_3$, which calculated for components is:
C = 56.69%: H = 10.67%: Si = 12.05%.
The product was analyzed to contain:
C = 56.88%: H = 10.42%: Si = 12.07%.

The above-described products obtained from each of the foregoing examples were tested for viscosity, flash point, weight loss, and wear scar, as reported in Table I below. The viscosity index (ASTM D 22 70) is an expression of the effect of temperatures on the viscosity of the product. The wear scar test is performed with a four ball 40 kg load apparatus at 1800 rpm and 168° F for 1 hour. The results, shown in Table I, establish the favorable functional fluid properties of the invented double cluster compounds.

TABLE I
PROPERTIES OF ALKOXYSILANE ESTER CLUSTER COMPOUNDS

| Compound | Viscosity CS -65° F | Viscosity CS 100° F | Viscosity CS 210° F | Viscosity Index | Flash Point SETA ° F | Weight Loss % at 400° F 1 Hr. | Scar Four Ball 1200 rpm mm |
|---|---|---|---|---|---|---|---|
| Product of Example I | 518.61 | 9.94 | 3.59 | 312 | 340 | 45.9 | 0.99 |
| Product of Example II | 791.82 | 10.92 | 3.84 | 317 | 360 | 20.5 | 1.04 |

I claim:
1. A compound having the formula:

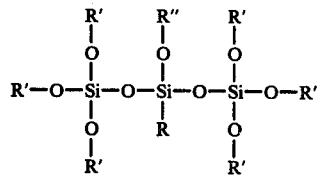

wherein R is hydrogen, an alkyl, alkenyl, aryl or aralkyl group, and R″ and the R′ groups are independently selected from alkyl, alkenyl, aryl and aralkyl with the proviso that at least a majority of the R′ radicals are sterically hindered alkyl groups having at least 3 carbon atoms.

2. The compound of claim 1 wherein R is hydrogen, an alkyl or alkenyl having about 1 to about 18 carbon atoms or an aryl or aralkyl having about 6 to about 24 carbon atoms, and each R′ and R″ is independently selected from alkyl or alkenyl having about 1 to about 24 carbon atoms or aryl or aralkyl having about 6 to about 24 carbon atoms subject to the proviso that at least a majority of the R′ groups are sterically hindered alkyl groups having about 3 to about 24 carbon atoms.

3. The compound of claim 2 wherein R is hydrogen, an alkyl or alkenyl having about 1 to about 8 carbon atoms or an aryl or aralkyl having about 6 to about 14 carbon atoms, and each R′ and R″ is independently selected from alkyl or alkenyl having about 1 to about 12 carbon atoms or an aryl or aralkyl having about 6 to about 14 carbon atoms, subject to the proviso that at least a majority of the R' groups are sterically hindered alkyl groups having about 4 to about 12 carbon atoms.

4. The compound of claim 3 wherein R" and the R' groups are independently selected from sterically hindered alkyl groups having about 4 to about 12 carbon atoms.

5. The compound of claim 4 wherein R is alkyl of about 1 to about 8 carbon atoms, and each R' and R" is independently selected from sterically hindered alkyl groups having about 4 to about 12 carbon atoms.

6. The compound of claim 5 wherein R is methyl and R" and R' are sec butyl.

7. A method of preparing the compound of claim 1 comprising:
reacting a halogenated alkoxysilane cluster compound of the formula:

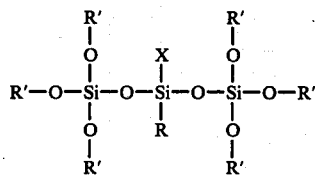

wherein X is a halogen and R and R' are as defined in claim 1,
with an alcohol of the formula:

R"—OH wherein R" is as defined in claim 1, in the presence of an acceptor base compound,
said reaction being conducted at a temperature ranging from about −30° C to about the reflux temperature of the lowest boiling reaction mixture ingredient.

8. The method of claim 7 wherein X is Cl, R is hydrogen, an alkyl or alkenyl having about 1 to about 18 carbon atoms or an aryl or aralkyl having about 6 to 24 carbon atoms and each R' and R" is independently selected from alkyl, alkenyl, aryl, or aralkyl subject to the proviso that at least a majority of the R' groups are sterically hindered alkyl groups having from 3 to about 24 carbon atoms.

9. The method of claim 8 wherein R is hydrogen, an alkyl or alkenyl having about 1 to about 8 carbon atoms or an aryl or aralkyl having about 6 to about 14 carbon atoms, and each R' is independently selected from alkyl, alkenyl, aryl or aralkyl subject to the proviso that at least a majority of the R' groups are sterically hindered alkyl groups having from about 4 to about 12 carbon atoms.

10. The method of claim 9 wherein X is Cl, R is alkyl of about 1 to about 8 carbon atoms, and R' and R" are independently selected from sterically hindered alkyl groups having about 4 to about 12 carbon atoms.

11. The method of claim 7 wherein the hydrogen halide acceptor base compound is present in an amount ranging from about 0.7 to about 6.0 moles per mole of alkoxysilane cluster compound reactant.

12. The method of claim 11 wherein the hydrogen halide acceptor base compound is present in an amount ranging from about 1.1 to about 1.3 moles per mole of alkoxysilane cluster compound reactant.

13. The method of claim 11 wherein the reaction is conducted at a temperature ranging from about 20° to about 80° C.

14. The method of claim 7 wherein the reaction is conducted in a non-protonic solvent medium.

* * * * *